United States Patent
Dib

(10) Patent No.: US 8,647,311 B2
(45) Date of Patent: Feb. 11, 2014

(54) BIOLOGICS INFUSION SYSTEM

(75) Inventor: Nabil Dib, Paradise Valley, AZ (US)

(73) Assignee: Translational Biologic Infusion Catheter, LLC, Gilbert, AZ (US)

( * ) Notice: Subject to any disclaimer, the term of this patent is extended or adjusted under 35 U.S.C. 154(b) by 702 days.

(21) Appl. No.: 12/563,876

(22) Filed: Sep. 21, 2009

(65) Prior Publication Data

US 2011/0071496 A1    Mar. 24, 2011

(51) Int. Cl.
*A61M 5/00*    (2006.01)

(52) U.S. Cl.
USPC .......... 604/246; 604/103.11; 604/103.13; 604/257; 604/508; 604/509; 604/522

(58) Field of Classification Search
USPC ......... 604/506, 507, 508, 509, 510, 513, 522, 604/103.01, 103.03, 103.11, 103.12, 604/103.13, 257, 258, 264, 93.01, 96.01, 604/246

See application file for complete search history.

(56) References Cited

U.S. PATENT DOCUMENTS

| | | | |
|---|---|---|---|
| 4,608,984 A | 9/1986 | Fogarty | |
| 5,156,594 A | 10/1992 | Keith | |
| 5,354,279 A | 10/1994 | Hofling | |
| 5,447,497 A * | 9/1995 | Sogard et al. | 604/101.02 |
| 6,319,248 B1 | 11/2001 | Nahon | |
| 6,394,978 B1 | 5/2002 | Boyle | |
| 6,524,302 B2 | 2/2003 | Kelley | |
| 6,579,287 B2 | 6/2003 | Wittenberger et al. | |
| 2006/0030814 A1 | 2/2006 | Valencia et al. | |
| 2007/0106208 A1 * | 5/2007 | Uber et al. | 604/65 |

FOREIGN PATENT DOCUMENTS

WO    2008057370 A2    5/2008

* cited by examiner

*Primary Examiner* — Theodore Stigell
(74) *Attorney, Agent, or Firm* — Nydegger & Associates

(57) ABSTRACT

A system for moving particles suspended in a first fluid, and for infusing them into the stream of a second fluid, includes a catheter with a multi-lumen distal tip. The tip is formed with a plurality of parallel lumens, wherein each lumen has a predetermined diameter. Importantly, the diameter of each lumen is dimensioned to sequentially receive particles therethrough, to prevent the particles from flocculating before they enter the stream of the second fluid. A valve, affixed to the outside of the catheter, can be provided to regulate flow of the second fluid and thereby facilitate entry of the particles into the stream of the second fluid.

20 Claims, 1 Drawing Sheet

BIOLOGICS INFUSION SYSTEM

FIELD OF THE INVENTION

The present invention pertains generally to infusion systems for introducing particles into a fluid stream. More particularly, the present invention pertains to infusion systems for introducing (infusing) particles of biological matter (e.g. stem cells) into the vasculature of a patient. The present invention is particularly, but not exclusively useful as a system using a multi-lumen filter that allows particles to enter a lumen of the filter either individually or in small groupings, for subsequent infusion into the vasculature of a patient.

BACKGROUND OF THE INVENTION

An introduction of particles into the vasculature of a patient requires simultaneously satisfying several different concerns or considerations. Depending on the type of particles involved, a concern of significant importance involves preventing the particles from flocculating, i.e. clumping together, as they are being infused or introduced into the vasculature. This is of particular concern in the case of stem cells which can flocculate, but which are most effective in therapy if left to function either as individual cells or in small groups of cells.

In all types of intravascular therapy (i.e. intracoronary, intra-arterial or intravenous), it is always an essential concern that the therapeutic agent (e.g. biologics or drugs) be infused or delivered in a predictably controlled manner. Furthermore, it is important that the therapeutic agent be effectively delivered to a proper destination in the vasculature. All of this involves dosage and delivery rate considerations. Moreover, it requires careful handling of the therapeutic agent to insure it (the therapeutic agent) is not damaged or otherwise compromised during an infusion.

From a mechanical perspective, it is known that the diameter of a fluid passageway is a factor that will affect the rate of fluid flow through the passageway. For protocols where small groups of de-flocculated particles are to be infused into a vessel of a vasculature, the diameter of the passageway must obviously be large enough to individually accommodate the small groups of particles. On the other hand, it must also be small enough to separate and prevent larger groups of particles (cells) from clinging to each other. A consequence of this is that the rate at which particles can be carried through the passageway will be circumscribed by the dimensions of the passageway. A further consequence of this is that, as particles leave the passageway, they are then influenced by the flow of fluid (i.e. blood) in the vessel of the vasculature. Depending on the purpose of the protocol, this may mean that the downstream fluid flow in the vasculature will somehow also need to be regulated.

In light of the above, it is an object of the present invention to provide an infusion system that can effectively introduce only small groups of particles into a fluid flow. Another object of the present invention is to provide an infusion system that coordinates the flow rate of a particle/fluid medium (i.e. a first fluid) with the flow rate of a fluid (i.e. a second fluid) into which the particle/fluid medium is being introduced. Yet another object of the present invention is to provide an infusion system that is easy to use, is simple to manufacture and is comparatively cost effective.

SUMMARY OF THE INVENTION

In accordance with the present invention, an infusion system includes an elongated catheter which is formed with a central lumen that extends between the proximal and distal ends of the catheter. Preferably, the catheter is tubular shaped with a smooth circular outer surface and, for purposes of description, the catheter defines a longitudinal axis. A source of a fluid medium having particles suspended therein (i.e. a particle/fluid medium) is connected in fluid communication with the proximal end of the catheter, and a tip (filter) is connected at the distal end of the catheter. For purposes of the present invention, the tip (filter) is provided to prevent the particles from flocculating as they are infused or introduced into a vessel in the vasculature of a patient. As envisioned for the present invention, the particles can be either biologics (i.e. cell, gene or protein) or drugs. And, they can be introduced into the vasculature for intracoronary, intra-arterial, or intravenous therapy.

Structurally, the tip is formed with a plurality of parallel lumens. Thus, with the tip affixed to the distal end of the catheter, each lumen of the tip is individually placed in fluid communication with the central lumen of the catheter. Importantly, each individual lumen is dimensioned to sequentially receive only small groups of particles (i.e. less than ten) therethrough. Specifically, although each lumen can receive several particles at a time, each lumen is sufficiently small to effectively separate particles from clinging to each other as they are received into the lumen. It follows that the system also includes a means for moving the particle/fluid medium through the lumen of the catheter, for further movement of the particles in alignment through individual lumens of the tip. For purposes of the present invention the means for moving this particle/fluid medium can be any such means well known in the pertinent art, such as an IV pole, a syringe, or a pump.

In addition to the tip (filter) described above, the system of the present invention also includes a configurable (inflatable) valve. Specifically, the configurable valve is positioned on the outer surface of the catheter to surround the catheter at a location that is proximal to the tip. Further, the valve is formed with a plurality of apertures that are arranged around the axis of the catheter. The purpose of these apertures is to control the axial movement of a fluid (e.g. blood) past the catheter in a distal direction substantially parallel to the axis of the catheter. This control is preferably provided by an inflator that selectively constricts the apertures of the valve to control the flow rate of fluid through the apertures.

In a preferred embodiment of the present invention, the valve is formed as an annulus that is centered on the axis. With this structure, the annulus has an inner diameter that is affixed to the outer surface of the catheter. The valve also has a substantially non-compliant material positioned on the outer periphery of the annulus that maintains the outer diameter at a predetermined radial distance from the catheter when the valve is inflated into a base configuration. Aside from the non-compliant material, the rest of the annulus is made of a compliant material. Importantly, this compliant material is responsive to the inflator to selectively constrict the apertures. Thus, in operation, an additional inflation of the valve beyond its base configuration substantially maintains the outer diameter at the predetermined radial position, while incrementally constricting the apertures.

Additional features of the present invention include a provision for positioning the catheter in the vasculature over a monorail type guide wire. Also, a fluid flow controller can be provided to meter fluid flow from the source into the central lumen of the catheter at a selected fluid pressure.

BRIEF DESCRIPTION OF THE DRAWINGS

The novel features of this invention, as well as the invention itself, both as to its structure and its operation, will be best

DESCRIPTION OF THE PREFERRED EMBODIMENTS

Figure 1:
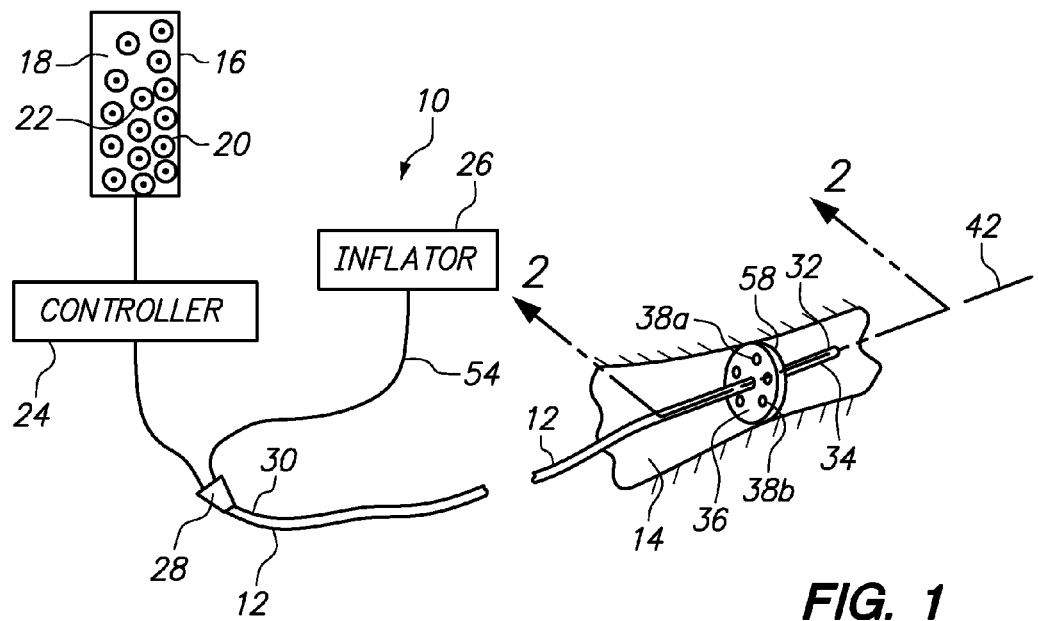
FIG. 1 is a schematic/perspective view of the system of the present invention shown with the system catheter positioned in an operational environment.

Referring initially to FIG. 1 a system for introducing (infusing) a fluid in accordance with the present invention is shown and is generally designated 10. As shown, the system 10 includes a catheter 12 that can be advanced into a vessel 14 to position the catheter 10 at a predetermined location in the vasculature of a patient (not shown). For the purposes of the present invention, the vessel 14 is preferably an artery or a vein in the cardiovascular system of a patient, and the system 10 is used for an intra-arterial, intravenous or intracoronary protocol.

In detail, FIG. 1 shows that the system 10 includes a source 16 for holding a fluid medium 18. As also shown in FIG. 1, a plurality of particles 20 are suspended in the fluid medium 18 to create a particle/fluid medium 22. For the present invention, the particles 20 may be some form of a drug or, most likely, they will be some form of a biologics (i.e. cell, gene or protein). In any event, the particles 20 will be suspended in the particle/fluid medium 22 for transport from the source 16 through the system 10 and into the vessel 14. As mentioned above for the system 10, the source 16 can be a syringe of a type well known in the pertinent art. FIG. 1 also shows that the system 10 includes a controller 24 that is in fluid communication with the source 16. As envisioned for the present invention, the controller 24 can be any type device that is known in the pertinent art for moving a fluid (e.g. the particle/fluid medium 22) through a fluid flow system (e.g. system 10). In general, such a device may be an IV pump, an IV pole or some other fluid flow metering apparatus. For an embodiment of the system 10 wherein the source 16 is a syringe, however, there is no specific need for a controller 24.

FIG. 1 also shows that the system 10 includes an inflator 26 for a purpose to be discussed below. When both the controller 24 and the inflator 26 are used for the system 10, they can be individually joined at a connector 28 to, respectively, establish separate fluid communication channels with the catheter 12. Preferably, as shown, this connector 28 is connected in fluid communication with the proximal end 30 of the catheter 12.

Still referring to FIG. 1, it is seen that the system 10 includes a tip (filter) 32 that is affixed to the distal end 34 of the catheter 12. Further, it is seen that a valve 36 is mounted on the catheter 12 proximal the distal end 34, and that the valve 36 is formed with a plurality of apertures, of which the apertures 38a and 38b are exemplary. The actual construction of the distal portion of the catheter 12, and the cooperation of structure between the tip (filter) 32 and the valve 36 will perhaps be best appreciated with reference to FIG. 2.

Figure 2:
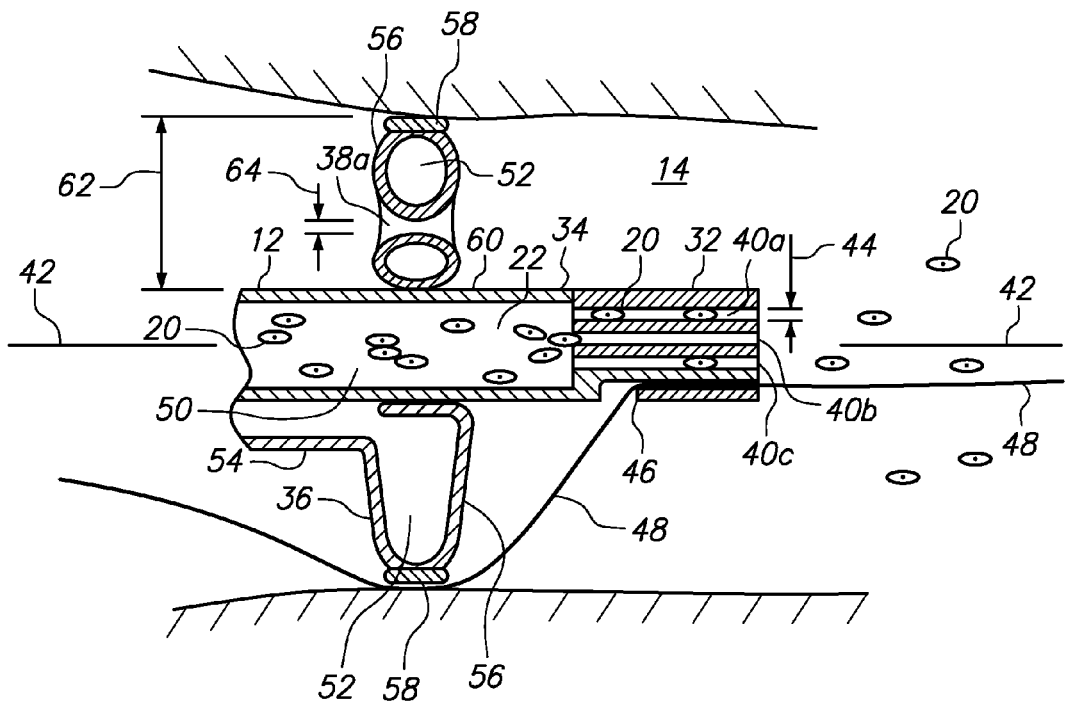
FIG. 2 is a cross-section view of the tip (filter) and distal portion of the system catheter as seen along the line 2-2 in FIG. 1.

Referring to FIG. 2, and with specific reference to the tip (filter) 32, it will be seen that the tip (filter) 32 is formed with a plurality of lumens, of which the lumens 40a, 40b, and 40c are exemplary. More specifically, the lumens extend axially through the tip (filter) 32 and are substantially parallel to each other. They are also substantially parallel to the axis 42 that is generally defined by the catheter 12. Importantly, each lumen is established with a diameter 44 that is specifically dimensioned to receive only individual or small groups of particles 20. Although each lumen can receive several de-flocculated particles 20 at a time, the individual particles 20 or small groups of particles remain separated while they transit the lumen (e.g. see lumen 40a). Further, the tip (filter) 32 can be formed with a monorail lumen 46 that will interact with a guide wire 48, in a manner well known by the skilled artisan, for the purpose of positioning the catheter 12 within the vessel 14.

With the structure of the tip (filter) 32 in mind, as described above, it is an important aspect of the present invention that the diameter 44 of each lumen be dimensioned to prevent the entry of large groups of flocculated particles 20 into the lumen from the central lumen 50 of the catheter 12. In particular, for different therapeutic protocols, it may be very necessary that the particles 20 be dispersed as they enter the vessel 14, to thereby minimize the possibility of subsequent flocculation in the vessel 14.

Recall, the valve 36 is formed with a plurality of apertures. Further, with cross reference to FIG. 1 and FIG. 2, it will also be appreciated that, when inflated, the valve 36 is generally shaped as an annulus and is formed with an inflation chamber 52. As shown, the inflation chamber 52 is connected in fluid communication with the inflator 26 via an inflation line 54. Within this structure, the inflation line 54 can be integrated into the catheter 12. For operational purposes, the valve 36 includes a valve body 56 that is made of a compliant, inflatable material. The valve 36 also includes a rim 58 made of a substantially non-compliant material that is located on the periphery of the annulus shaped valve 36. For the system 10, the valve 36 is located proximal to the tip (filter) 32, and it is affixed to the outer surface 60 of the catheter 12 by any means known in the pertinent art, such as by gluing or bonding.

Operationally, the valve 36 starts from a deflated configuration, and it is then inflated by the inflator 26 into a base configuration (see FIGS. 1 and 2) wherein the valve 36 is constrained by the rim 58. In this base configuration, the valve 36 will extend from the surface 60 of catheter 12 through a radial distance 62 and, in the base configuration, it will most likely make contact with the vessel 14. Also, in the base configuration, each aperture (e.g. aperture 38a) will have a diameter 64. With an additional inflation of the valve 36 by the inflator 26, however, two different structural consequences occur. For one, the rim 58 does not expand from the base configuration. Thus, the radial distance 62 remains substantially constant. For another, the valve body 56 will expand in response to the inflator 26 such that the apertures are incrementally constricted. Stated differently, and with specific reference to the aperture 38a, the diameter 64 will be diminished. In an alternate embodiment for the present invention, there may be no need for the valve 36.

For an operation of the system 10 in an intra-arterial, intravenous or intracoronary protocol, a guide wire 48 is first prepositioned in the vasculature of a patient. The guide wire 48 is then received into the monorail lumen 46 of the catheter 12, and the catheter 12 is advanced over the guide wire 48 and into position in the vasculature of the patient. Once the catheter 12 has been properly positioned, the valve 36 is inflated into its base configuration, or beyond. The exact extent of inflation for valve 36 will depend on the desired flow rate for fluid through the apertures in the vessel 14. With the valve 36 inflated, the controller 24 is then activated to cause a flow of particle/fluid medium 22 from the source 16 and through the central lumen 50 of the catheter 12. As particles 20 in the particle/fluid medium 22 arrive at the tip (filter) 32, the respective diameters 44 of individual lumens in the tip (filter)

32 allow only individual particles 20 or small groups of particles 20 to enter the lumen. Thus, the flocculation of particles 20 in the central lumen 50 is disrupted, and flocculation of the particles 20 after they have passed through the tip (filter) 32 is minimized. Although the above discussion has focused on applications of the system 10 within the cardiovascular system of a patient, the system 10 is appropriate for any use wherein particles 20 may be suspended in a particle/fluid medium 22 for subsequent release as individual particle 20 into a fluid flow (e.g. blood flow through a vessel 14).

While the particular Biologics Infusion System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An infusion system which comprises:
    an elongated catheter formed with a central lumen extending between a proximal end and a distal end;
    a source of a fluid medium having particles suspended therein, wherein the source is connected in fluid communication with the proximal end of the catheter;
    a tip defining an axis and formed with a plurality of parallel lumens extending through the tip in an axial direction, wherein the tip is affixed to the distal end of the catheter to individually place each lumen of the tip in fluid communication between the central lumen and a vessel of a patient, and wherein each individual lumen is dimensioned to sequentially receive a portion of the fluid medium containing suspended particles therethrough, and wherein each lumen is sufficiently small to effectively separate the particles from clinging to each other as the particles are received into the lumen; and
    a device for moving the fluid medium with suspended particles through the lumen of the catheter, for further movement of the particles in alignment through individual lumens of the tip.

2. A system as recited in claim 1 wherein the catheter has an outer surface and is tubular shaped to define an axis, and wherein the system further comprises:
    a configurable valve positioned on the outer surface of the catheter to surround the catheter at a location proximal to the tip, wherein the valve is formed with a plurality of apertures arranged around the axis of the catheter to allow for axial movement of a fluid through the apertures and on past the catheter in a distal direction substantially parallel to the axis of the catheter; and
    an inflator for selectively configuring the valve to control the flow rate of fluid through the apertures.

3. A system as recited in claim 2 wherein the valve is formed as an annulus centered on the axis with an inner diameter conformed to the outer surface of the catheter, and wherein the valve is inflatable into a base configuration wherein an outer diameter is established at a predetermined radial distance beyond the outer surface of the catheter, and further wherein an additional inflation of the valve substantially maintains the outer diameter while incrementally constricting the apertures.

4. A system as recited in claim 3 wherein the annulus comprises:
    a compliant material responsive to the inflator to selectively constrict the apertures; and
    a substantially non-compliant material positioned on a periphery of the annulus to maintain the outer diameter at the predetermined radial distance from the outer surface of the catheter during a constriction of the apertures.

5. A system as recited in claim 3 further comprising a guide wire selectively engaged with the tip to position the tip in a vasculature vessel of a patient.

6. A system as recited in claim 5 wherein the inflator is operated to maintain valve contact with the vessel when the valve is in its base configuration.

7. A system as recited in claim 1 wherein the particles are selected from a group consisting of agents useful for gene therapy, drug therapy and protein therapy.

8. A system as recited in claim 1 wherein the particles are stem cells.

9. A system as recited in claim 1 wherein the device is a fluid flow controller positioned to meter fluid flow from the source into the central lumen of the catheter.

10. A system for introducing particles suspended in a first fluid into a second fluid flowing through a substantially tubular shaped vessel, the system comprising:
    a source of the particles suspended in the first fluid;
    a substantially cylindrical shaped separator in fluid communication with the particle source, wherein the separator defines an axis and is formed with a plurality of longitudinally aligned, parallel lumens, with each lumen dimensioned to receive a portion of the first fluid containing suspended particles therethrough, and wherein the separator is positionable in the vessel;
    a configurable valve positioned around the separator and affixed thereto, with the valve extending radially outward from the separator so as to come into contact with the vessel, wherein the valve is formed with a plurality of apertures arranged around the axis of the separator to allow for axial movement of the second fluid through the apertures in a direction substantially parallel to the axis of the separator;
    a device for moving particles from the source, through the separator, and into the vessel; and
    an inflator for selectively configuring the valve, wherein the inflator incrementally constricts the apertures to control the flow rate of the second fluid through the apertures as particles emerge from the separator for introduction into the second fluid.

11. A system as recited in claim 10 further comprising a catheter with a central lumen for interconnecting the particle source with the separator, wherein the catheter has an inner surface and an outer surface.

12. A system as recited in claim 11 wherein the valve is formed as an annulus centered on the separator axis with an inner diameter conformed to the outer surface of the catheter, and wherein the valve is inflatable into a base configuration wherein an outer diameter is established at a predetermined radial distance from the catheter, and further wherein an additional inflation of the valve substantially maintains the outer diameter while incrementally constricting the apertures.

13. A system as recited in claim 12 wherein the annulus comprises:

a compliant material responsive to the inflator to selectively constrict the apertures; and a substantially non-compliant material positioned on a periphery of the annulus to maintain the outer diameter at the predetermined radial distance from the outer surface of the catheter during a constriction of the apertures.

14. A system as recited in claim 12 wherein the inflator is operated to maintain valve contact with the vessel when the valve is in its base configuration.

15. A system as recited in claim 11 wherein the device is a fluid flow controller positioned to meter fluid flow from the source into the central lumen of the catheter.

16. A system as recited in claim 10 wherein the particles are selected from a group consisting of agents useful for gene therapy, drug therapy and protein therapy.

17. A system as recited in claim 10 wherein the particles are stem cells.

18. A method for introducing particles suspended in a first fluid into a second fluid flowing through a substantially tubular shaped vessel, the method comprising the steps of:

provide a source of the particles suspended in the first fluid;

connecting a substantially cylindrical shaped separator in fluid communication with the particle source through a catheter having an outer surface and formed with a central lumen, wherein the separator defines an axis and is formed with a plurality of longitudinally aligned, parallel lumens extending through the separator in an axial direction between the central lumen and the vessel, with each lumen dimensioned to receive a portion of the first fluid containing suspended particles therethrough, and wherein the separator is positioned in the vessel, and further wherein a configurable valve is positioned around the separator and affixed thereto, with the valve extending radially outward from the separator and into contact with the vessel, wherein the valve is formed with a plurality of apertures arranged around the axis of the separator to allow for axial movement of the second fluid through the apertures in a direction substantially parallel to the axis of the separator;

positioning the separator in the vessel; and inflating the valve, wherein inflation of the valve incrementally constricts the apertures to control the flow rate of the second fluid through the apertures as particles emerge from the separator for introduction into the second fluid.

19. A method as recited in claim 18 wherein the valve is formed as an annulus centered on the separator axis with an inner diameter conformed to the outer surface of the catheter, and the method further comprises the steps of:

inflating the valve into a base configuration wherein an outer diameter is established at a predetermined radial distance from the catheter; and performing an additional inflation of the valve to substantially maintain the outer diameter while incrementally constricting the apertures.

20. A method as recited in claim 18 wherein the particles are stem cells.

* * * * *